US007653235B2

(12) United States Patent
Mylaraswamy et al.

(10) Patent No.: US 7,653,235 B2
(45) Date of Patent: Jan. 26, 2010

(54) SURFACE ANOMALY DETECTION SYSTEM AND METHOD

(75) Inventors: Dinkar Mylaraswamy, Fridley, MN (US); Russell D. Braunling, Eden Prairie, MN (US)

(73) Assignee: Honeywell International Inc., Morristown, NJ (US)

( * ) Notice: Subject to any disclaimer, the term of this patent is extended or adjusted under 35 U.S.C. 154(b) by 732 days.

(21) Appl. No.: 11/261,066

(22) Filed: Oct. 27, 2005

(65) Prior Publication Data
US 2007/0098245 A1    May 3, 2007

(51) Int. Cl.
*G06K 9/00*    (2006.01)
*G06K 9/48*    (2006.01)
*G06K 9/40*    (2006.01)
(52) U.S. Cl. .................. 382/141; 382/199; 382/260
(58) Field of Classification Search ............ 382/141, 382/199, 260
See application file for complete search history.

(56) References Cited
U.S. PATENT DOCUMENTS

| | | | |
|---|---|---|---|
| 4,484,081 A | | 11/1984 | Cornyn, Jr. et al. |
| 4,603,584 A | | 8/1986 | Bartle et al. |
| 5,442,462 A | | 8/1995 | Guissin |
| 5,549,002 A | * | 8/1996 | Chiao et al. ............ 73/602 |
| 5,571,966 A | | 11/1996 | Tsuboi |
| 5,648,613 A | * | 7/1997 | Kiefer ................... 73/611 |
| 5,698,787 A | | 12/1997 | Parzuchowski et al. |
| 5,760,904 A | | 6/1998 | Lorraine et al. |
| 6,038,335 A | * | 3/2000 | Yokoyama et al. ....... 382/141 |
| 6,128,092 A | * | 10/2000 | Levesque et al. ........ 356/451 |
| 6,182,512 B1 | | 2/2001 | Lorraine |
| 6,245,016 B1 | * | 6/2001 | Daft et al. .............. 600/443 |
| 6,285,449 B1 | | 9/2001 | Ellingson et al. |
| 6,487,909 B2 | | 12/2002 | Harrold et al. |
| 6,490,927 B2 | | 12/2002 | Braunling et al. |
| 6,592,523 B2 | | 7/2003 | Avinash et al. |
| 6,606,909 B2 | | 8/2003 | Dubois et al. |

(Continued)

OTHER PUBLICATIONS

Kegl, B. Krzyzak, A. Linder, T. Zeger, K. "Learning and design of principal curves", IEEE Transactions on Pattern Analysis and Machine Intelligence, vol. 22, No. 3, Mar. 2000.*
Rene Sicard, Jacques Goyette, Djamel Zellouf, A SAFT algorithm for lamb wave imaging of isotropic plate-like structures, Dec. 4, 2001.

(Continued)

*Primary Examiner*—Samir A. Ahmed
*Assistant Examiner*—Li Liu
(74) *Attorney, Agent, or Firm*—Ingrassia Fisher & Lorenz, P.C.

(57) ABSTRACT

A system and method is provided to detect surface anomalies. The detection system and method provides the ability to automatically detect and characterize anomalies on a surface, such as detecting and characterizing pitting corrosion on metal surfaces. The surface anomaly detection system and method uses an image of the surface under evaluation. The image data is passed to a noise filter. The noise filter uses an estimated characterization of the background noise to remove the background noise from the image data. The smoothed pixel intensity is then compared to a threshold to identify significant departures. The detected anomalies are then passed to a contour detector, which determines the contours of anomalies in the surface to provide more precise characterization of the detected anomalies. The detected closed contours of anomalies may then be passed to a defect severity estimator that provides an anomaly factor metric.

18 Claims, 4 Drawing Sheets

U.S. PATENT DOCUMENTS

| | | | |
|---|---|---|---|
| 6,771,807 B2 * | 8/2004 | Coulombe et al. | 382/149 |
| 6,775,400 B1 | 8/2004 | Zhao et al. | |
| 6,792,357 B2 | 9/2004 | Menon et al. | |
| 6,831,469 B2 | 12/2004 | Foreman et al. | |
| 6,870,950 B2 | 3/2005 | Houge et al. | |
| 6,874,365 B2 | 4/2005 | Deveney et al. | |
| 7,286,964 B2 * | 10/2007 | Kim | 702/183 |

OTHER PUBLICATIONS

Jeffrey D. Banfield and Adrian E. Raftery, Ice Flow Identification In Satellite Images Using Mathematical Morphology And Clustering About Principal Curves, 1992.

Irving S. Reed, Adaptive Multiple-Bank CFAR Detection Of An Optical Pattern With Unknown Spectral Distribution, 1990.

* cited by examiner

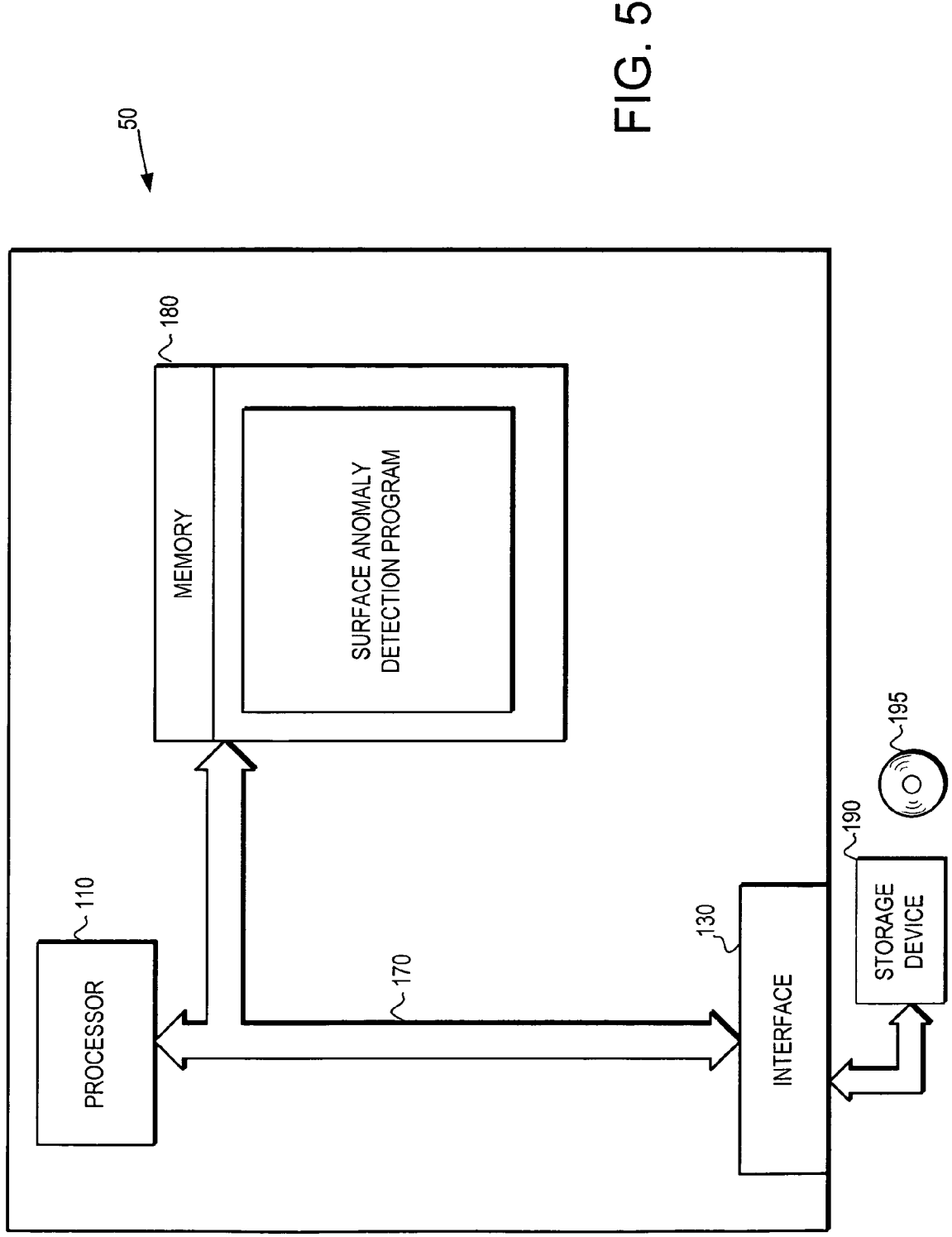

SURFACE ANOMALY DETECTION SYSTEM AND METHOD

FIELD OF THE INVENTION

This invention generally relates to diagnostic systems, and more specifically relates to the detection of surface anomalies such as corrosion and other types of physical defects.

BACKGROUND OF THE INVENTION

There are many applications where it is of critical importance to determine the amount of degradation that is or has occurred on a device. For example, in modern manufacturing techniques it can be critical for efficient manufacturing to know whether physical degradation, such as corrosion, is occurring on critical surfaces. As another example, in aircraft engines, the surface integrity of turbine blades is of extreme importance to safe and reliable operation. In all of these applications there is a strong need for effective techniques to determine if surface anomalies have formed, or are being formed on a device.

One particularly serious type of surface anomaly is pitting corrosion. Generally, pitting is a localized form of corrosion that is characterized by the formation of holes or pits on the surface. Pits often have a small surface area, and can thus be difficult to accurately detect or characterize. However, pits can penetrate to a relatively large depth and can thus cause severe failures in some applications.

Additionally, in some applications there is also a strong need to determine the size and rate of the growth of surface anomalies. For example, determining the rate of pitting corrosion growth can be used to calculate the structural integrity and hence the remaining component lifetime, a process generally referred to as component lifing. Without an accurate determination of the rate of anomaly growth may not be possible to determine the remaining component life.

Unfortunately, previous techniques for detecting surface anomalies in general, and pitting corrosion in particular, have had limited usefulness because they typically require an expert evaluation to interpret the data. This prevents, for example, the system from being used in an automatic feedback control loop. Thus, what is needed is a robust automated system and method for detecting and characterizing pitting corrosion and other surface anomalies.

BRIEF SUMMARY OF THE INVENTION

The embodiments of the present invention provide a surface anomaly detection system and method. The detection system and method provides the ability to automatically detect and characterize anomalies on a surface. For example, the detection system and method may be particularly applicable to detecting and characterizing pitting corrosion on metal surfaces.

The surface anomaly detection system and method uses an image of the surface under evaluation. A variety of different types of sensors and methods can be used to obtain the image. As one example technique, the image data comprises data created using a synthetic aperture focusing technique (SAFT). This technique applies guided waves to the surface under evaluation. For example, the waves are guided using a piezoelectric transducer array. In this embodiment, the guided waves are reflected back to the transducer by the physical defects in the material. The reflected waves received by each of the transducers in the array are delayed and summed on an individual frequency basis to create an image of the scanned region. The image indicates regions of high intensity that correspond to surface anomalies, and regions of low intensity that correspond to normal surfaces.

The image data is passed to a noise filter. The noise filter uses an estimated characterization of the background noise to remove the background noise from the image data. In one embodiment, the background noise is removed by using a stochastic model to estimate a smoothed value for the intensity at each pixel. In one specific implementation, the estimate from the stochastic model is implemented using a modified Kalman filter.

The smoothed pixel intensity is then compared to a threshold to identify significant departures. In one embodiment, the threshold detector uses a threshold calculated using a constant false positive rate. In this embodiment, a desired constant false positive rate is selected and used to determine the threshold value for each of the pixels in the image, and the threshold can then be used to establish the distribution of anomalies in the image data.

The detected anomalies are then passed to a contour detector, which determines the contours of anomalies in the surface to provide more precise characterization of the surface defects. In one embodiment, the detected anomalies are joined together by drawing closed contour boundaries around the anomalies. This groups anomalies together that may all be part of the same surface defect. In one specific implementation, the contour boundaries are identified using a principle curves technique that removes islands of noise from the data. This results in closed contours that encompass the detected anomalies.

The detected closed contours of anomalies may then be passed to a surface defect severity estimator. The defect severity estimator provides a metric referred to herein as an anomaly factor. Specifically, the defect estimator can estimate the severity of the surface anomaly by calculating a parameter of the closed contour. For example, the anomaly factor can be expressed as the area of the closed contour together with a center. In another embodiment, the defect severity estimator can aggregate the area of closed contours at the same location calculated over a length of time to determine the rate of change in the detected anomalies. These different characterizations of the anomalies can then be used to determine the extent of the structural damage and its likely impact on the associated device.

The foregoing and other objects, features and advantages of the invention will be apparent from the following more particular description of a preferred embodiment of the invention, as illustrated in the accompanying drawings.

BRIEF DESCRIPTION OF DRAWINGS

The preferred exemplary embodiment of the present invention will hereinafter be described in conjunction with the appended drawings, where like designations denote like elements, and:

FIG. 5 is a schematic view of an exemplary computer system.

DETAILED DESCRIPTION OF THE INVENTION

The embodiments of the present invention provide a surface anomaly detection system and method. The detection system and method provides the ability to automatically detect and characterize surface anomalies on a surface under test. While the surface anomaly detection system and method can be used for a variety of anomalies, the system and method may be particularly applicable to detecting and characterizing pitting corrosion and material cracks.

Figure 1:
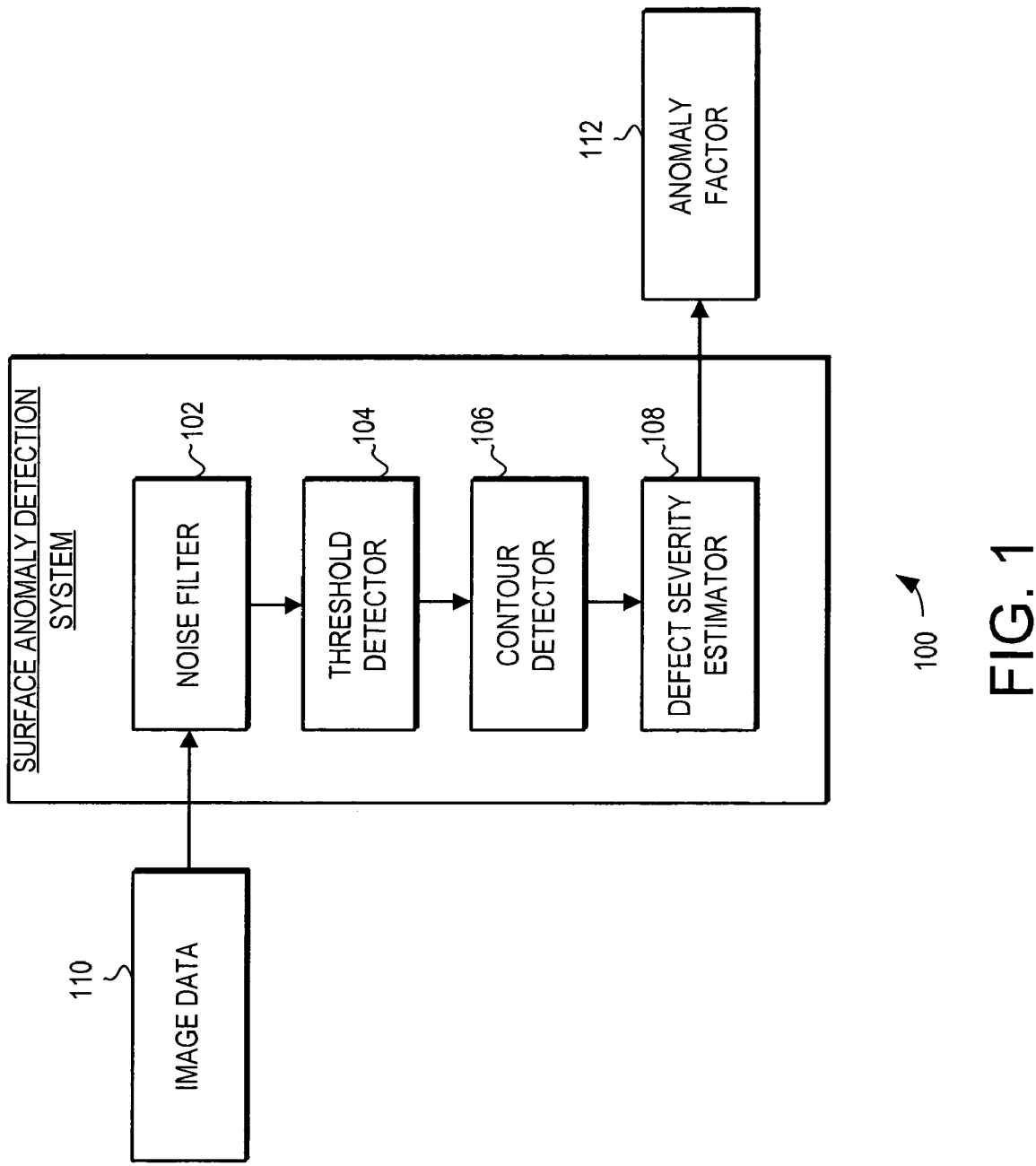
FIG. 1 is a schematic view of a surface anomaly detection system.

Turning now to FIG. 1, a schematic view of surface anomaly detection system 100 is illustrated. The surface anomaly detection system 100 includes a noise filter 102, a threshold detector 104, a contour detector 106, and a defect severity estimator 108. In general, the surface anomaly detection system 100 receives image data 110 of a surface under evaluation and processes the image data to calculate an anomaly estimate 112 for the surface under the evaluation. A variety of different types of sensors and method can be used to obtain the image data 110. As one example technique, the image data 110 comprises data created using a synthetic aperture focusing technique (SAFT). As will be discussed in greater detail below, this technique applies guided waves to the surface under evaluation. For example, the waves are guided using a piezoelectric transducer array. In this embodiment, the guided waves are reflected back to the transducer by the physical defects in the material. The reflected waves received by each of the transducers in the array are delayed and summed on an individual frequency basis to create the image data 110 of the scanned surface under test. When so created, the image data 110 indicates regions of high intensity that correspond to surface anomalies, and regions of low intensity that correspond to normal surfaces.

The image data 110 is passed to the noise filter 102. The noise filter 102 suitably uses an estimated characterization of the background noise to remove the background noise from the image data. In one embodiment, the background noise is removed by using a stochastic model to estimate a smoothed value for the intensity at each pixel. In one specific implementation, the stochastic model is implemented in the noise filter 102 using a modified Kalman filter. The removal of the noise results in smoothed image data that can then be used to locate surface anomalies.

The smoothed image data is then passed to the threshold detector 104. The threshold detector compares each pixel in the image data to a threshold value(s) to identify significant intensity departures. In one embodiment, the threshold detector 104 uses a threshold calculated using a constant false positive rate. In this embodiment, a desired constant false positive rate is selected and used to determine the threshold value for each of the pixels in the image which can then be used establish the distribution of anomalies in the image data.

The detected anomalies are then passed to the contour detector 106, which determines the contours of anomalies in the surface to provide more precise characterization of the detected anomalies. In one embodiment, the detected anomalies are joined together by drawing closed contour boundaries around the anomalies. This technique combines anomalies together that may be all part of the same surface anomaly. In one specific implementation, the contour detector 106 defines boundaries using a principle curves technique that removes islands of noise from the data. This results in closed contours that encompass the detected anomalies.

The detected closed contours of anomalies are then passed to a defect severity estimator 108. The defect severity estimator 108 generates an anomaly factor 112. The anomaly factor 112 is a metric that can be used to characterize and quantify the severity of a defect. In one embodiment, the defect estimator 108 can generate the anomaly factor 112 by a parameter of the closed contour(s) located in the image data. For example, by calculating an area along with a center from the closed contour. In another embodiment, the defect severity estimator 108 can aggregate the area of multiple closed contours corresponding to the same surface anomaly taken at different times to determine the rate of change in the detected anomalies, and calculate the anomaly factor 112 based on the rate of change. In both cases, the characterizations of the anomalies provided by the anomaly factor 112 can then be used to determine the extent of the structural damage and its likely impact on the associated device.

As described above, the surface anomaly detection system 100 receives image data of the surface under test. In one embodiment, the image data is created using a synthetic aperture focusing technique (SAFT). This technique applies guided waves to the surface under evaluation. For example, the waves are guided using a piezoelectric transducer array. In this embodiment, the guided waves are reflected back to the transducer by the physical defects in the material. The reflected waves received by each of the transducers in the array are delayed and summed on an individual frequency basis to create an image of the scanned region. The image indicates regions of high intensity that correspond to surface anomalies, and regions of low intensity that correspond to normal surfaces. There are several other devices and approaches that can be used to induce the guided waves into the material and to receive the reflected waves. These include Electromagnetic Acoustic Transducers (EMAT), magneto-restrictive transducers and laser based systems. More information about how SAFT can be used to create the image of the surface under test can be found at Sicard, R., J. Goyette, D. Zellouf (2002) "A SAFT Algorithm for Lamb Wave Imaging of Isotropic Plate-Like Structures". Ultrasonics, 39, 7: 487-494.

The image data can be created and stored in a variety of formats. In one suitable format, the image data is in the form of a red-green-blue (RGB) image of the surface. For example, regions of high intensity reflected waves, which are indicative of surface anomalies, can be indicated by colors with significant red components. Conversely, regions of low intensity can be indicated by colors with significant blue components. Of course, this is just one type of exemplary format in which the image data can be stored.

Figure 2:
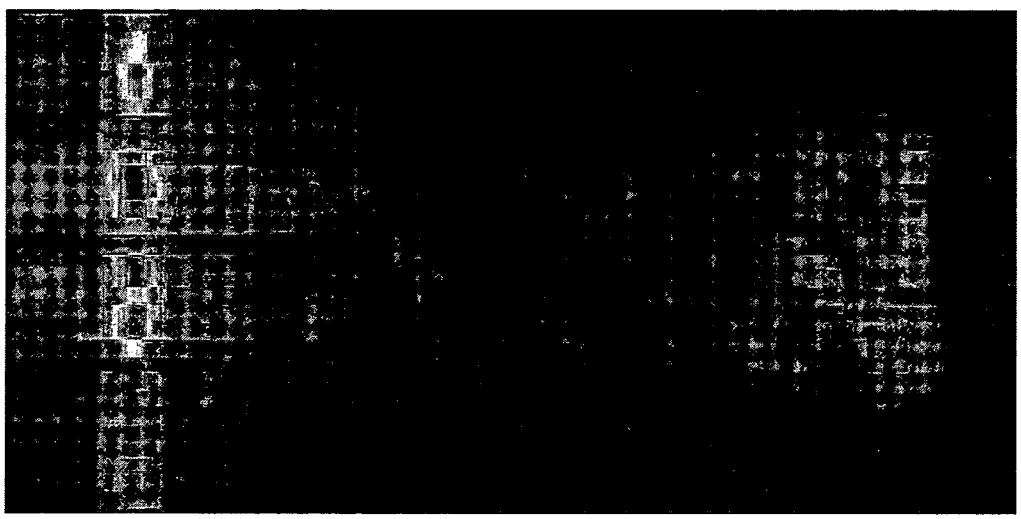
FIG. 2 is a graphical view of an exemplary image.

Turning now to FIG. 2, an exemplary image is illustrated in graph 200. Graph 200 illustrates an image where lighter areas correspond to areas of greater intensity. Of course, this is just one example of image data. For example, in other applications the intensity would be illustrated using a color RGB representation.

One issue with image data created using a SAFT technique is that the image data is often very noisy. In this case the high intensity regions of the image may indicate noise caused by manufacturing and sensing irregularities rather than surface anomalies. The noise filter 102 provides an automated mechanism for eliminating noise from the image data. The noise filter 102 determines the mean intensity of the image data, where the mean intensity, also referred to herein as the smoothed intensity, is defined as the intensity after the noise has been at least substantially removed. In this application, the subscript i,j is used to denote the pixel element at location i,j. The intensity of each image element (e.g., a pixel or collection of pixels) can then be modeled as:

$$x_{i,j} = \bar{x}_{i,j} + \epsilon_{i,j} \qquad \text{Equation 1.}$$

where $x_{i,j}$ is the observed (noisy) intensity of the element at the i,j location, $\bar{x}_{i,j}$ is the mean value of the intensity of the element at the i,j, and $\epsilon_{i,j}$ is the background noise at i,j. Conceptually, the noise filter 102 calculates the mean pixel intensity $\bar{x}_{i,j}$ at a location i,j by taking the noisy image data and subtracting a "background noise component".

Several different techniques can be used for determining and modeling the background noise component $\epsilon_{i,j}$. The background noise component $\epsilon_{i,j}$ can be characterized using experimentation. For example, by taking multiple images of clean samples with no surface anomalies, the noise in typical images can be calculated and characterized. This characterization of the noise may then be used to implement the filter, which is then used in operation to filter image data from surfaces under examination. Additionally, several different techniques can be used to characterize the noise $\epsilon_{i,j}$ using multiple images.

Several specific examples of noise characterization techniques will now be discussed. In one example, no noise is assumed to exist and $\epsilon_{i,j}$ is thus equal to a 0, $\forall_{i,j}$. In another example, a constant noise is assumed to exist and $\epsilon_{i,j}$ is a constant, $\forall_{i,j}$. In this embodiment, 0 is valid value for the constant, implying a noise free background. In this embodiment the noise subtracted from the observed intensity to calculate the corresponding mean intensity value at location i,j. In another example, the statistical characteristics of noise is assumed to be uniform such that $\epsilon_{i,j} = N(0, \sigma)$, $\forall_{i,j}$. In this notation, N stands for a Gaussian distribution with mean 0 and standard deviation $\sigma$. In this model the background noise is assumed to belong to a single distribution with the same mean and variance. Thus, the background noise is assumed to vary spatially, although at each location the distribution is well characterized. The standard deviation $\sigma_{i,j}$ can be calculated using $x_{i,j}$ observations from multiple image data.

All of these techniques provide a mechanism for modeling the noise that can be used to filter the image data and calculate the mean intensity value $\bar{x}_{i,j}$. It should however also be noted that in some implementations the background noise is not modeled explicitly. Instead, in some techniques the noise filter directly determines the mean intensity value of image at each location i, j using a suitable technique. For example, by averaging the intensity of neighboring pixels. As one specific example, the neighborhood may comprise of eight pixels that surround the pixel at location i,j. The intensity of these neighboring pixels is averaged to create a smoothed mean value of the pixel intensity at location i,j. In another example, the intensity of these neighboring pixels may be weighted to calculate the mean intensity at location i,j. In this example, special neighborhood definitions would typically be specified for edge pixels.

In another embodiment, the mean intensity $\bar{x}_{i,j}$ is calculated using a stochastic model. In this model, $\bar{x}_{i,j}$ can be assumed to be an unobservable or hidden state evolving in time, where at each time t a noisy observation of this state is obtained. In this embodiment, the mean intensity $\bar{x}_{i,j}$ is represented as the output of a linear dynamic system excited by independent and uncorrelated random signal. For example, the mean intensity can be presented as:

$$\bar{x}_{i,j} = a\bar{x}_{i,j} + q_{i,j}(t) \qquad \text{Equation 2}$$

where $q_{i,j}(t)$ is a random input variable with zero mean and known variance Q, a is a time constant of the process which characterizes how fast the intensity may change with respect to time. Multiple sets of image data may be collected over a series of time interval. For example, the pixel intensity at location i,j from image collected at time t may provide the noisy observation of the hidden state at time t, with the state itself is evolving according to equation 2.

A noise filter based on a stochastic model is implemented using a modified Kalman filter. In general, a Kalman filter is a statistical estimator used to separate random noise from an underlying signal. In this approach the underlying signal (i.e., the pixel intensity $\bar{x}_{i,j}$ at pixel i,j) is represented as the output of a linear dynamical system defined in equation 2 and excited by independent or uncorrelated noise $\epsilon_{i,j}(t)$ following a Gaussian distribution. The Kalman filter thus provides a mechanism can that can obtain the mean intensity value $\bar{x}_{i,j}$ and hence separate it from the noise.

In one specific embodiment of the invention the basic Kalman filter is modified to account for the non-Gaussian nature of the random variable $q_{i,j}(t)$. For example, the Kalman filter is modified to account for a $q_{i,j}(t)$ that follows a Weibull distribution. In this embodiment the Kalman filter is modified to follow the random variable $q_{i,j}(t)$ up to its first two moments. For example, the Kalman filter is modified to replace $q_{i,j}(t)$ with another random variable $p_{i,j}(t) \sim N(m, v)$ such that the mean (i.e., the $1^{st}$ moment) of $q_{i,j}(t)$ is equal to the mean of $p_{i,j}(t)$, and the variance (i.e., the $2^{nd}$ moment) of $q_{i,j}(t)$ is equal to the mean of $p_{i,j}(t)$. In this embodiment, the original Kalman filter equations are re-derived following this approximation. Thus, the Kalman filter is modified such that the underlying dynamic system is excited by non-Gaussian white noise measure, allowing the Kalman filter to obtain the mean intensity value $\bar{x}_{i,j}$ and hence separate it from the noise.

Implementing such a modified Kalman filter generally involves two steps. Step one is a prediction step. Given a linear dynamic model, such as the model described by equation 2, one can predict the value of the state at t+1 given its value at t. In other words, it can predict $\bar{x}_{i,j}(t+1)$ from $\bar{x}_{i,j}(t)$. Then at time t+1, a noisy value $\bar{x}_{i,j}(t+1)$ is obtained for the pixel intensity at location i,j. The difference between the prediction at step t+1 from equation (2) and the measurement at time t+1 is called the innovation or the error term. The second step involves updating the state based on this error term. In other words, the prediction of $\bar{x}_{i,j}(t+1)$ is updated. A typical Kalman filter does this by combining all the information content of all measurements made till time t+1 and equation (2) to produce an optimal estimate for $\bar{x}_{i,j}(t+1)$, where optimality is defined in the statistical sense and in simple words it means that the total mean error at t+2 will be smaller than the total mean error at t+1.

A variety of different techniques can be used to implement a Kalman filter. For example, a series of image data from clean samples is used to identify the "a" and the covariance of the random variable in equation 2. This step can be referred to as system identification. In one example, the parameters of equation 2 are identified using a least squares minimization. In this example, the innovation error (difference between what equation 2 predicts and actual intensity observation at location i,j) is minimized subject to optimal values of "a" and "Q".

The modified Kalman filter can thus be implemented to work as a Stochastic filter and calculate the mean value for each pixel in the data. This provides the ability to characterize a noise distribution without assuming that it has a particular type of distribution (e.g, Gaussian.) Thus, the modified Kalman filter is one mechanism that can be used to calculate the mean value for the intensity of each pixel $\bar{x}_{i,j}$ in the data, removing noise and smoothing the image data.

The smoothed image data is then passed to the threshold detector 104 to identify significant variations in the intensity of the image. In general, threshold detector compares the mean or smoothed intensity at each pixel $\bar{x}_{i,j}$ against a pre-defined baseline and looks for statistically significant departures. Pixel locations i,j where the image data crosses a threshold value are indicative of anomalies in the image data.

As one example, the baseline threshold value is set to a pre-determined constant δ. In this example, if the mean intensity $\bar{x}_{i,j}$ at location i,j exceeds δ, then an anomaly is declared at that location. In this case, a variety of factors can be used to determine the appropriate value of δ. For example, if $\bar{x}_{i,j}=0$ indicates "blue color or defect free pixel" and $\bar{x}_{i,j}=1$ indicates "red color or significant surface anomaly", and the threshold δ can be set such that all locations that have an intensity of 0.9 or greater are considered as anomaly. That is, $$r_{ij} = \bar{x}_{ij} - \delta; A_{i,j} = 1 \text{ if } r_{ij} > 0 \text{ else } A_{ij} = 0 \quad \text{Equation 3}$$

In this case the residual $r_{i,j}$ is defined for each pixel as the difference between the mean intensity value $\bar{x}_{i,j}$ and the pre-defined threshold δ. $A_{i,j}$ is an anomaly value corresponding to the pixel at the i,j location. The threshold detector sets the anomaly value $A_{i,j}$ for each pixel to indicate whether an anomaly was located at that pixel location i,j. In equation 3, the anomaly value is set to 1 if the residual $r_{i,j}$ is greater than 0, else it is assigned a value of 0.

In a second embodiment, the threshold detector uses a constant false positive probability technique. In this example, experimentation using samples, commonly referred to as coupons, is used determine the distribution of the mean intensity $\bar{x}_{i,j}$. In this example, the mean intensity values from all pixel locations in group of images are aggregated, and a distribution of the residual value is generated. This distribution is then used to determine the threshold values for anomaly detection. For example, an anomaly is detected when the residual $r_{i,j}$ exceeds some pre-defined multiple of the distribution standard deviation. In this embodiment, the threshold δ is set based on the area under the residual $r_{i,j}$ distribution. In other words, the threshold is determined to meet a pre-defined false positive criterion. Stated another way, δ=b·s, where s is the standard deviation of the residual distribution and is determined by collating $\bar{x}_{i,j}$ from all pixel locations collected from multiple image data. For example, if b=6 (six sigma), then the probability of a false positive of detecting an anomaly is $10^{-6}$.

In a third embodiment, the threshold detector uses a constant false positive rate technique to determine the threshold value. In general, a false positive rate is defined as the number of false positives per successful detection of an anomaly. To achieve a desired false positive rate, calibration is performed using samples with varying degrees of anomalies. The calibration samples are analyzed to determine a value for the threshold that achieves the desired rate.

Figure 3:
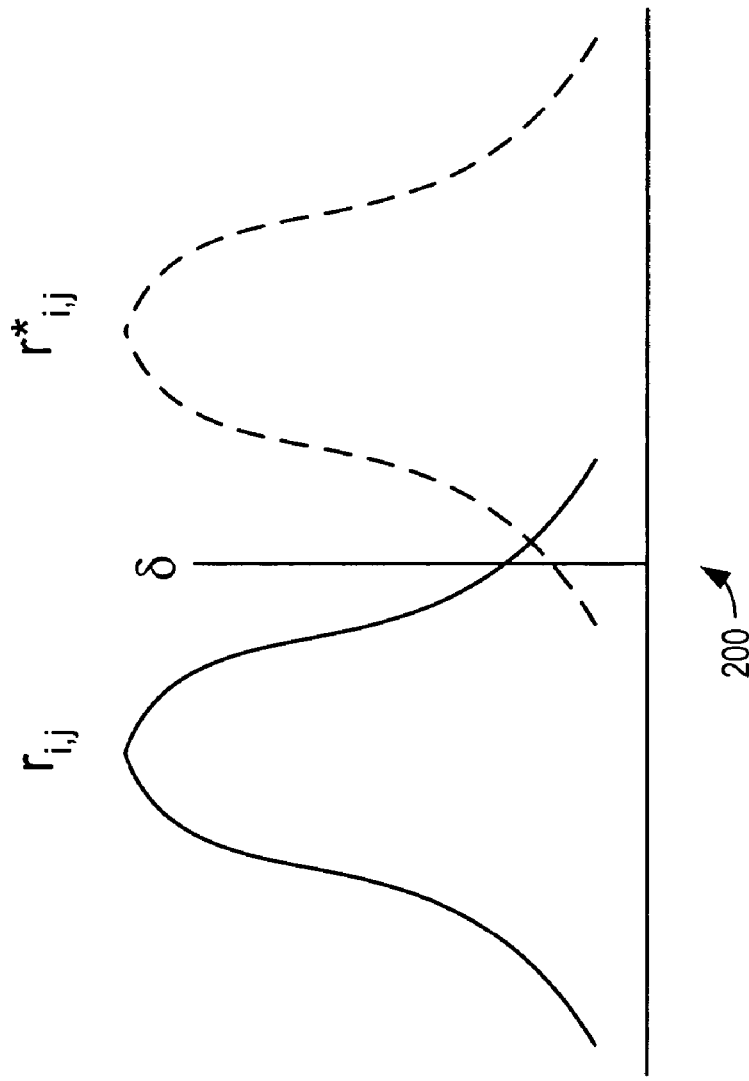
FIG. 3 is a graphical view of exemplary residuals used to determine a threshold.

In this embodiment, the $\bar{x}_{i,j}$ values from all pixel locations are collected from multiple images that exhibit confirmed structural defect. Other $\bar{x}_{i,j}$ values from are collected from multiple images of clean samples. The two sets of mean intensity values $\bar{x}_{i,j}$, one corresponding to pixels that do not have any defect, and the other set corresponding to pixel locations that have a confirmed defect, are used to generate two residual distributions that can the be used to determine a threshold value using a constant false positive rate technique. Turning now to FIG. 3, a statistical distribution of residuals that can be used to determine a threshold is illustrated. Specifically, graph 200 illustrates the distribution of the residual for several "good" calibration samples $r_{i,j}$ (illustrated with a solid line) and the distribution of residual for several samples with surface anomalies $r^*_{i,j}$ (illustrated with a dotted line). In a constant false positive rate technique, the threshold δ is determined such that a selected false positive rate is met for each pixel. As can be seen in graph 200, the distribution for good residuals $r_{i,j}$ and the anomaly residuals $r^*_{i,j}$ may overlap at the center. This overlap indicates an area where the residual values from surfaces under test will be ambiguous with regards to indicating anomalies.

As stated above, a constant false positive rate technique uses calibration results from good and corroded samples to select a threshold δ that will result in the desired rate of false positives. Stated another way, the threshold δ will be set such that the corroded residual $r^*_{i,j}$ area to the left of the threshold δ will have a desired ratio to the area of the good residual $r^*_{i,j}$ area to the right of threshold δ. When so calculated using sufficient numbers of known good and samples with confirmed anomalies, the threshold δ can then be used for detecting pixels with excessive intensity levels. This provides a threshold δ that minimizes the probability of false classification while maintaining a pre-defined detection probability. Thus determined, the threshold δ can be used in the threshold detector to determine when intensity values cross the threshold δ such that pixels with excessive intensity are detected.

The pixels with excessive intensity that were detected by the threshold detector are then passed to the contour detector, which determines the contours of anomalies in the surface to provide a more precise characterization of the detected anomalies. The main objective of the contour detector is to establish the boundaries of the excessive intensity pixel cluster and thus provide a less ambiguous output for the detection of anomalies. In one embodiment, the detected anomalies are joined together by drawing closed contour boundaries around the identified pixels. This combines pixels together that are all part of the same cluster or surface defect, e.g., all part of one corrosion pit. In one specific implementation, the contour detector defines boundaries using a principle curves technique that removes islands of noise from the data. This results in closed contours that encompass the detected cluster of pixels.

As one example, the input to the contour detector comprises a matrix with rows representing discrete positions along the length of the surface under investigation, while the columns representing discrete positions along the width of the surface. The contour detector takes this matrix input and outputs a smooth continuous curve along the outer rim of the excessive intensity pixel cluster.

In one specific embodiment the contour is modeled as a principal curve. A principal curve is a flexible family of one-dimensional non-parametric curves which pass through the middle of a d-dimensional probability distribution of 0 and 1 pixel intensity values generated during the threshold step. Several different techniques can be used to calculate the principal curves from a given data set of pixel intensity values. For example, one technique for calculating a principal curve is Polygon Line Algorithm. This technique starts with a straight line segment (a part of the first principal component line or the least squares regression line), and in each iteration it increases the number of line segments by adding a vertex to the polygonal line produced by the previous iteration. After adding the vertex, the position of each vertex is updated in an inner loop. Typically the technique will continue until the number of vertices exceeds a predetermined limit.

The inner loop includes of a projection step and an optimization step. In the projection step the data points are partitioned into "nearest neighbor regions" according to which segment or vertex they project. In the optimization step the new position of each vertex is determined in a line search to minimize an objective function that consists an average squared distance term and a curvature penalty. These two steps are iterated until convergence is achieved. Thus, the contour detector can use an iterative technique to draw a polygon that passes through the mean of the pixels that exceed the threshold.

Figure 4:
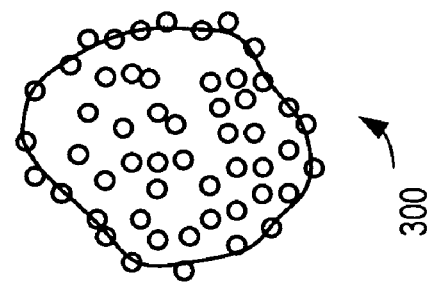
FIG. 4 is a graphical view of exemplary closed contour defined around anomaly values.

Thus, the principal curve technique identifies edges clustered around the principal curve. Each identified cluster then corresponds to a possible anomaly and the corresponding principal curve is the estimated outline or contour of the anomaly. Turning now to FIG. 4, a graph 300 of exemplary processed image data included in a matrix with i,j locations corresponding to pixels with excessive intensity as detected by the threshold detector. FIG. 4 shows a principal curve is generated from the image data that provides a contour that is indicative of the outline of the anomaly cluster.

In this technique it will generally be desirable to define a minimum size of the anomaly that will be identified for further evaluation. Typically, the minimum size of an anomaly that will be identified needs to be translated into pixel count. For example, in one application a user may not care about anomalies that are less than 1 mm×1 mm. Based on the resolution of the image, this may correspond to n pixels. This number can thus be used to determine the minimum number of points that will be used to draw the polygon edges. This also prevents the principal curves from merely joining every pixel and generating a very noisy contour, such as a worst case polygon.

The detected closed contours of anomalies are then passed to a defect severity estimator that provides a metric referred to herein as an anomaly factor. The anomaly factor can then be used to calculate a magnitude for a surface defect under test. In one example, the anomaly factor can be used to characterize the growth rate of the anomalies by calculating the rate of change over time. As another example, the defect severity estimator can estimate the severity of the defect by calculating a parameter, such as the area, from the closed contours. These different characterizations of the anomalies can then be used to determine the extent of the surface anomaly and its likely impact on the associated device.

In one embodiment, the anomaly factor is calculated as the area enclosed by the principal curve defining the closed contour. The area can be calculated from principal curve using any suitable technique. In one example, if the principal curve is described by a n-polygon, then one can calculate the area of the circumscribing circle, where the circumscribing circle connects every vertex. In a second example, if the principal curve is described by a n-polygon, then one can calculate the area of the circum-inscribing circle, where the circum-inscribing circle is inside the polygon and is a tangent to every edge of the polygon.

In another embodiment, the principal curve is mapped as a regular geometric shape and the anomaly factor is selected to be a parameter of that shape. For example, the principal curve can be mapped to a circle and the diameter used as the anomaly factor.

In all these cases, the anomaly factor is selected to characterize the anomaly and provide a metric that can be used to evaluate the detected anomaly. Furthermore, multiple examinations of a surface under test can be used to trend the anomaly factor as a function of time. Such a time-series plot can be used to provide an end user with a quick summary of how the anomaly is progressing and thus can assist in determining the potential effects of future corrosion.

The surface anomaly detection system and method can be implemented using a variety of different platforms. Turning now to FIG. 5, an exemplary computer system 50 is illustrated. Computer system 50 illustrates the general features of a computer system that can be used to implement the invention. Of course, these features are merely exemplary, and it should be understood that the invention can be implemented using different types of hardware that can include more or different features. It should be noted that the computer system can be implemented in many different environments. The exemplary computer system 50 includes a processor 110, an interface 130, a storage device 190, a bus 170 and a memory 180. In accordance with the preferred embodiments of the invention, the memory system 50 includes a surface anomaly detection program.

The processor 110 performs the computation and control functions of the system 50. The processor 110 may comprise any type of processor, including single integrated circuits such as a microprocessor, or may comprise any suitable number of integrated circuit devices and/or circuit boards working in cooperation to accomplish the functions of a processing unit. In addition, processor 110 may comprise multiple processors implemented on separate systems. In addition, the processor 110 may be part of an overall vehicle control, navigation, avionics, communication or diagnostic system. During operation, the processor 110 executes the programs contained within memory 180 and as such, controls the general operation of the computer system 50.

Memory 180 can be any type of suitable memory. This would include the various types of dynamic random access memory (DRAM) such as SDRAM, the various types of static RAM (SRAM), and the various types of non-volatile memory (PROM, EPROM, and flash). It should be understood that memory 180 may be a single type of memory component, or it may be composed of many different types of memory components. In addition, the memory 180 and the processor 110 may be distributed across several different computers that collectively comprise system 50.

The bus 170 serves to transmit programs, data, status and other information or signals between the various components of system 100. The bus 170 can be any suitable physical or logical means of connecting computer systems and components. This includes, but is not limited to, direct hard-wired connections, fiber optics, infrared and wireless bus technologies.

The interface 130 allows communication to the system 50, and can be implemented using any suitable method and apparatus. It can include a network interfaces to communicate to other systems, terminal interfaces to communicate with technicians, and storage interfaces to connect to storage apparatuses such as storage device 190. Storage device 190 can be any suitable type of storage apparatus, including direct access storage devices such as hard disk drives, flash systems, floppy disk drives and optical disk drives. As shown in FIG. 5, storage device 190 can comprise a disc drive device that uses discs 195 to store data.

In accordance with the preferred embodiments of the invention, the computer system 50 includes the surface anomaly detection program. Specifically during operation, the surface anomaly detection program is stored in memory 180 and executed by processor 110. When being executed by the processor 110, the surface anomaly detection program receives image data of surfaces under test and generates an anomaly factor that is indicative the surface anomalies on the surface under test.

It should be understood that while the present invention is described here in the context of a fully functioning computer system, those skilled in the art will recognize that the mechanisms of the present invention are capable of being distributed as a program product in a variety of forms, and that the present invention applies equally regardless of the particular type of computer-readable medium used to carry out the distribution. Examples of computer-readable medium include: recordable media such as floppy disks, hard drives, memory cards and optical disks (e.g., disk 195).

The embodiments of the present invention thus provide a surface anomaly detection system and method. The surface anomaly detection system and method provides the ability to automatically detect and characterize corrosion and other anomalies on a surface. The embodiments and examples set forth herein were presented in order to best explain the present invention and its particular application and to thereby enable those skilled in the art to make and use the invention. However, those skilled in the art will recognize that the foregoing description and examples have been presented for the purposes of illustration and example only. The description as set forth is not intended to be exhaustive or to limit the invention to the precise form disclosed. Many modifications and variations are possible in light of the above teaching without departing from the spirit of the forthcoming claims.

The invention claimed is:

1. A surface anomaly detection system for detecting anomalies on a surface, the detection system comprising:
   a synthetic aperture focusing device, the synthetic aperture focusing device configured to apply guided waves to the surface and generate image data of the surface, the image data comprising a plurality of pixels;
   a noise filter, the noise filter configured to receive the image data of the surface, the noise filter configured to generate a mean value for each of the plurality of pixels, wherein the noise filter comprises a modified Kalman filter configured to implement a stochastic model to estimate the mean value of each of the plurality of pixels;
   a threshold detector, the threshold detector configured to receive the mean value for each the plurality of pixels, the threshold detector configured to evaluate the mean value for each of the plurality of pixels using a threshold to determine which of said plurality of pixels exceed the threshold;
   a contour detector, the contour detector configured to determine a contour of pixels that exceed the threshold using a principal curves technique; and
   a severity estimator, the severity estimator configured to calculate an anomaly factor based on a parameter of the contour.

2. The system of claim 1 wherein the synthetic aperture focusing device comprises a piezoelectric transducer array configured to receive reflected waves from the surface to create the image data.

3. The system of claim 1 wherein the modified Kalman filter comprises a Kalman filter modified such that the underlying dynamic system is excited by non-Gaussian white noise.

4. The system of claim 1 wherein the threshold value is determined using a constant false positive rate determined from a plurality of good samples and a plurality of samples with confirmed defects.

5. The system of claim 1 wherein the contour detector uses an iterative technique to draw a polygon that passes through the mean of the pixels that exceed the threshold.

6. The system of claim 1 wherein the severity estimator calculates the anomaly factor based on an area of the contour.

7. A method of detecting a surface anomaly on a surface, the method comprising:
   receiving image data of the surface, the image data created by a synthetic aperture focusing device configured to apply guided waves to the surface and generate the image data of the surface, the image data comprising a plurality of pixels; using a processor to perform the following steps:
   filtering the image data with a modified Kalman filter to generate a mean value for each of the plurality of pixels, wherein the modified Kalman filter is configured to implement a stochastic model to estimate the mean value of each of the plurality of pixels;
   evaluating the mean value for each of the plurality of pixels to determine which of said plurality of pixels exceed a threshold;
   determining a contour of pixels that exceed the threshold using a principal curves technique;
   calculating an anomaly factor based on a parameter of the contour of pixel: and
   generating an output indicative of the surface anomaly from the anomaly factor.

8. The method of claim 7 wherein the synthetic aperture focusing device comprises a piezoelectric transducer array configured to receive reflected waves from the surface to create the image data.

9. The method of claim 7 wherein the modified Kalman filter comprises a Kalman filter modified such that the underlying dynamic system is excited by non-Gaussian white noise.

10. The method of claim 7 wherein the threshold value is determined using a constant false positive rate determined from a plurality of good samples and a plurality of samples with confirmed defects.

11. The method of claim 7 wherein determining a contour of pixels that exceed the corresponding threshold comprises using an iterative technique to draw a polygon that passes through the mean of the pixels that exceed the threshold.

12. The method of claim 7 wherein calculating an anomaly factor based on a parameter of the contour of pixels comprises calculating the anomaly factor based on an area of the contour.

13. A program product comprising:
   a) a surface anomaly detection program for detecting anomalies on a surface, the surface anomaly detection program including:
      a noise filter, the noise filter receiving image data of the surface, the image data of the surface created using a synthetic aperture focusing technique, the image data comprising a plurality of pixels, the noise filter generating a mean value for each of the plurality of pixels, wherein the noise filter comprises a modified Kalman filter configured to implement a stochastic model to estimate the mean value of each of the plurality of pixels;
      a threshold detector, the threshold detector receiving the mean value for each the plurality of pixels, the threshold detector evaluating the mean value for each of the plurality of pixels using a threshold to determine which of said plurality of pixels exceed the threshold;
      a contour detector, the contour detector determining a contour of pixels that exceed the threshold using a principal curves technique; and
      a severity estimator, the severity estimator calculating an anomaly factor based on a parameter of the contour; and
   b) computer-readable storage medium storing said program.

14. The program product of claim 13 wherein the synthetic aperture focusing device comprises a piezoelectric transducer array configured to receive reflected waves from the surface to create the image data.

15. The program product of claim 13 wherein the modified Kalman filter comprises a Kalman filter modified such that the underlying dynamic system is excited by non-Gaussian white noise.

16. The program product of claim 13 wherein the threshold value is determined using a constant false positive rate determined from a plurality of good samples and a plurality of samples with confirmed defects.

17. The program product of claim 13 wherein the contour detector uses an iterative technique to draw a polygon that passes through the mean of the pixels that exceed the threshold.

18. The program product of claim 13 wherein the severity estimator calculates the anomaly factor based on an area of the contour.

* * * * *

UNITED STATES PATENT AND TRADEMARK OFFICE
CERTIFICATE OF CORRECTION

PATENT NO. : 7,653,235 B2  Page 1 of 1
APPLICATION NO. : 11/261066
DATED : January 26, 2010
INVENTOR(S) : Mylaraswamy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1124 days.

Signed and Sealed this

Twenty-third Day of November, 2010

David J. Kappos
*Director of the United States Patent and Trademark Office*